United States Patent [19]
Anderson

[11] Patent Number: 5,085,085
[45] Date of Patent: Feb. 4, 1992

[54] DIRECTIONAL SEDIMENT AND POLLUTION MONITOR

[76] Inventor: Roger Y. Anderson, 3201 Campus Blvd. NE., Albuquerque, N. Mex. 87106

[21] Appl. No.: 499,164

[22] Filed: Mar. 26, 1990

[51] Int. Cl.$^5$ .............................................. G01N 1/00
[52] U.S. Cl. ............................ 73/863.02; 73/864.63
[58] Field of Search ........... 73/863.02, 863.21, 863.23, 73/863.51, 863.52, 863.57, 864.63, 170 A, 863.01

[56] References Cited

U.S. PATENT DOCUMENTS

| | | | |
|---|---|---|---|
| 3,203,236 | 8/1965 | Prince | 73/170 A |
| 3,715,913 | 2/1973 | Anderson | 73/61.4 |
| 4,091,666 | 5/1978 | Niskin | 73/170 A |
| 4,321,823 | 3/1982 | Anderson | 73/61 R |
| 4,762,009 | 8/1988 | Scrudto | 73/863.23 |

FOREIGN PATENT DOCUMENTS 1288531 2/1987 U.S.S.R. ..................... 73/863.01

Primary Examiner—Robert Raevis

[57] ABSTRACT

A directional sediment and pollution monitor adapted to be positioned in the body of water. A baffle is positioned in the upper, open end of each collecting tube for minimizing turbulence in the collecting tube and to inhibit the escape of materials. Means are also provided for collecting samples at short time intervals, for measuring the compass heading of the framework structure and collecting tubes, and for measuring and recording changes in the compass heading over short and long interval of time.

7 Claims, 2 Drawing Sheets

DIRECTIONAL SEDIMENT AND POLLUTION MONITOR

BRIEF SUMMARY OF THE INVENTION

According to the present invention, there is provided a directional sediment and pollution monitor which is adapted to be positioned in a body of water and which comprises an array of vertically positioned collecting tubes oriented in the body of water with respect to compass bearing or direction. According to the present invention each collecting vessel is allowed to collect suspended materials carried in water by currents moving in a restricted and known geographic direction. As a result, only suspended materials moving along a known and restricted pathway enter each collecting vessel, thereby eliminating the need for many sampling stations to determine the source of materials carried by currents within said body of water. Not only does each collecting vessel measure the vector of sediment being transported by currents, each vessel collects a known volume of said materials and measures the volume and rate of movement of sediments and polluting substances. Accordingly, the present device makes it possible to identify the source of polluting substances, the pathways along which these substances move, and the rate at which such substances are being released and distributed in the body of water. The present directional sediment and pollution monitor thereby overcomes all of the problems discussed below with respect to prior art systems.

A collecting vessel or tube is located in each quadrant of the sediment-sampling device and a funnel-shaped collecting chamber is located at the center. The collecting tube in each quadrant consists of a closed lower end and an open upper end for collecting sediment that is carried past the tube by currents of water. The collecting tube in each quadrant is closed by a cap when the tube is oriented in a vertically aligned position. The collecting tube in each quadrant is hinged so that a flow of current rotates the collecting tube into the current from a closed position and allows sediment to accumulate in the tube.

It is therefore the object of the present invention to provide a novel directional sediment and pollution monitor.

It is a further object of the present invention to provide a sediment and pollution monitoring device for bodies of water that measures the direction of movement, the rate of movement, the accumulated volume, and the source of polluting substances and natural materials.

It is a still further object of the present invention to provide a directional sediment and pollution monitor including a device for collecting, protecting, and preserving sediment and polluting substances for the purpose of further study and analysis.

It is another object of the present invention to measure the direction, rate of movement, and volume of sediment and polluting substances during short and known time intervals and over extended periods of time.

Still other objects, features and attendant advantages of the present invention will become apparent to those skilled in the art from the reading of the following detailed description of the preferred embodiment constructed in accordance therewith, taken in conjunction with the accompanying drawings wherein like numerals designate like parts in the several figures and wherein:

DETAILED DESCRIPTION OF THE INVENTION

Description of the Prior Art

A wide variety of natural materials as well as substances that are by-products of human activities are carried into rivers, estuaries, bays, lagoons, lakes, and the oceans. Such materials generally remain suspended for some period of time before they eventually settle to the bottom of a water body. Some of these substances, such as mercury, lead, PCB's, are known to have a harmful effect on life or the condition of the water body. Also, by accumulating in the tissues of fish and other organisms, these substances may have a harmful effect on human life. The amount of potentially harmful substances that are accumulating in the water bodies of the world is creating a serious problem of pollution, whose magnitude is so great that many individuals, private institutions, and government agencies have called for regular programs of sampling and the monitoring of sediments and pollution to determine the level of pollution and to detect changes in the rate of pollution.

Present aquatic sampling and monitoring systems and devices have many problems associated therewith. The most common method for sampling the substances suspended in a body of water makes use of sampling bottles or sediment trapping devices that collect suspended materials at a particular location in the water body. However, such sampling methods and devices have several serious limitations and disadvantages therewith. Such sampling methods and devices measure only the general distribution of pollutants within the water body. The inability to measure the direction of movement means that it is very difficult to identify the source of a natural material or polluting substance. The only present means for determining the source and direction of movement of pollutants is by deploying many devices and collecting samples at a large number of spot-sampling stations and observing where pollutants occur in greatest concentration. The deployment of many devices requires the proportionate use of boats and trained personnel and distance of travel. The present practice of deploying many sampling device at many stations increases costs and discourages the investigation of many problems related to environmental pollution. In addition, the present method of spot-sampling does not measure the pathway, the volume, and the rate of movement of natural and polluting substances.

Figures 2, 3:
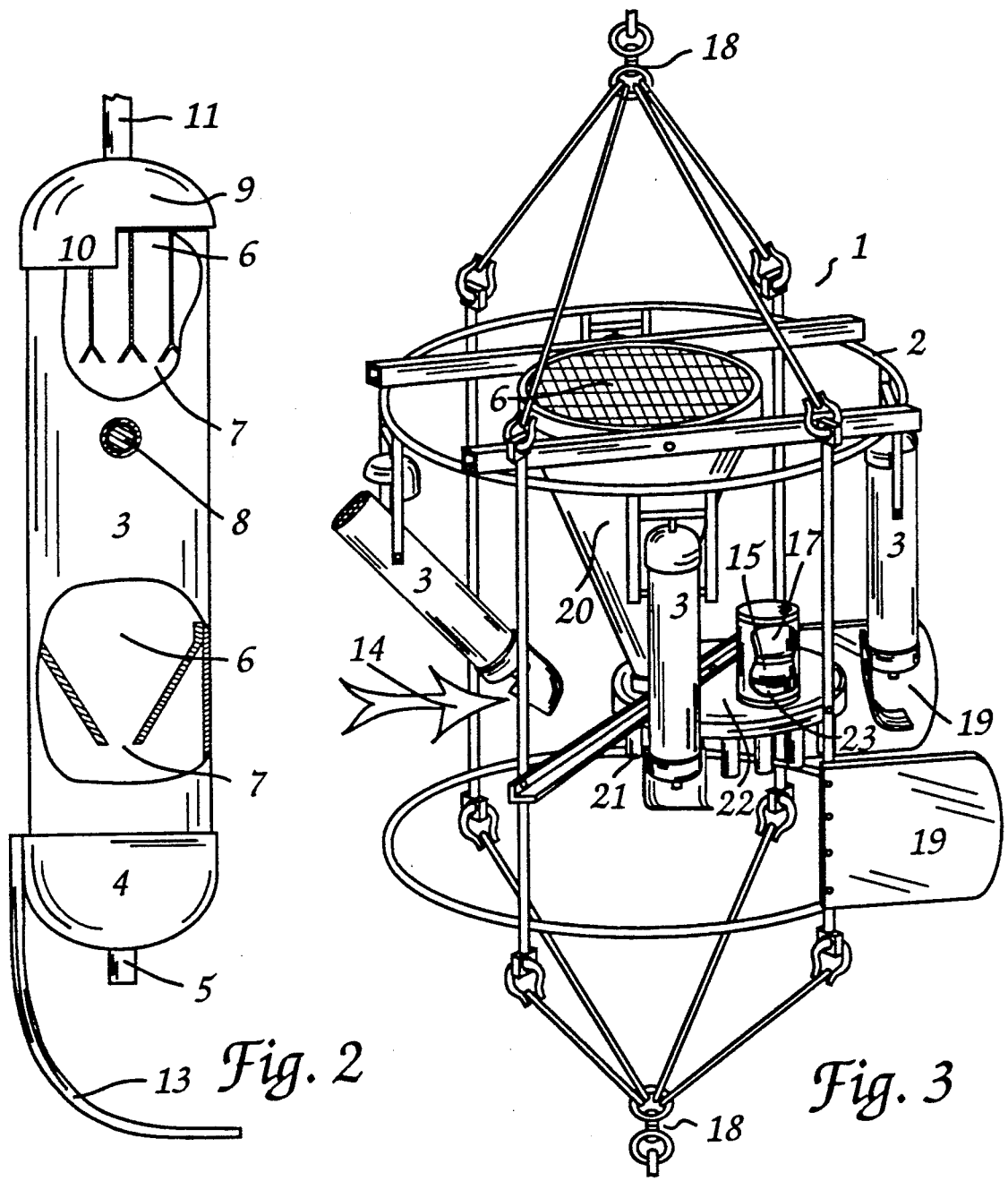
FIG. 2 is a side elevation of a single collecting chamber from one quadrant of the apparatus of FIG. 1, partially cut away to the centerline.
FIG. 3 is a perspective view of apparatus of FIG. 1 and structures for supporting the apparatus within a body of water and aligning the apparatus of FIG. 1 in a water current.

Referring to FIG. 2, sediment-vector tube 3 is generally aligned vertically and closed at the lower end by an end cap 4 and removable plug 5 for recovering the sample. Sediment-vector tube 3 is open at the upper end for receiving material suspended in the water body and contains a baffle 6 comprised of many tubular cells, each cell has an open upper end and contains an orifice 7 partly closing the lower end of each cell, for preventing entry of large organisms, reducing turbulence in the sediment-vector tube 3, and inhibiting the escape of materials upon recovery of the device. Sediment-vector tube 3 is mounted through its greatest diameter on a free swinging, tubular hinge bar 8. The upper, open end of the sediment-vector tube 3 is covered by a closing cap 9 that is configured to have a sediment-vector-tube stop 10 as an integral part of said closing cap.

Referring again to FIG. 1, closing cap 9 is rigidly mounted to a cap-mounting rod 11 that is rigidly affixed to a horizontal cross-member 12 of the framework structure 2. The sediment-vector tube 3 is affixed beneath the closing cap by the free-swinging tubular hinge bar 8 that is mounted between two vertical members of the framework structure 2. A curved, current-pressure vane 13 is affixed to the lower part of the sediment-vector tube 3.

Figure 1:
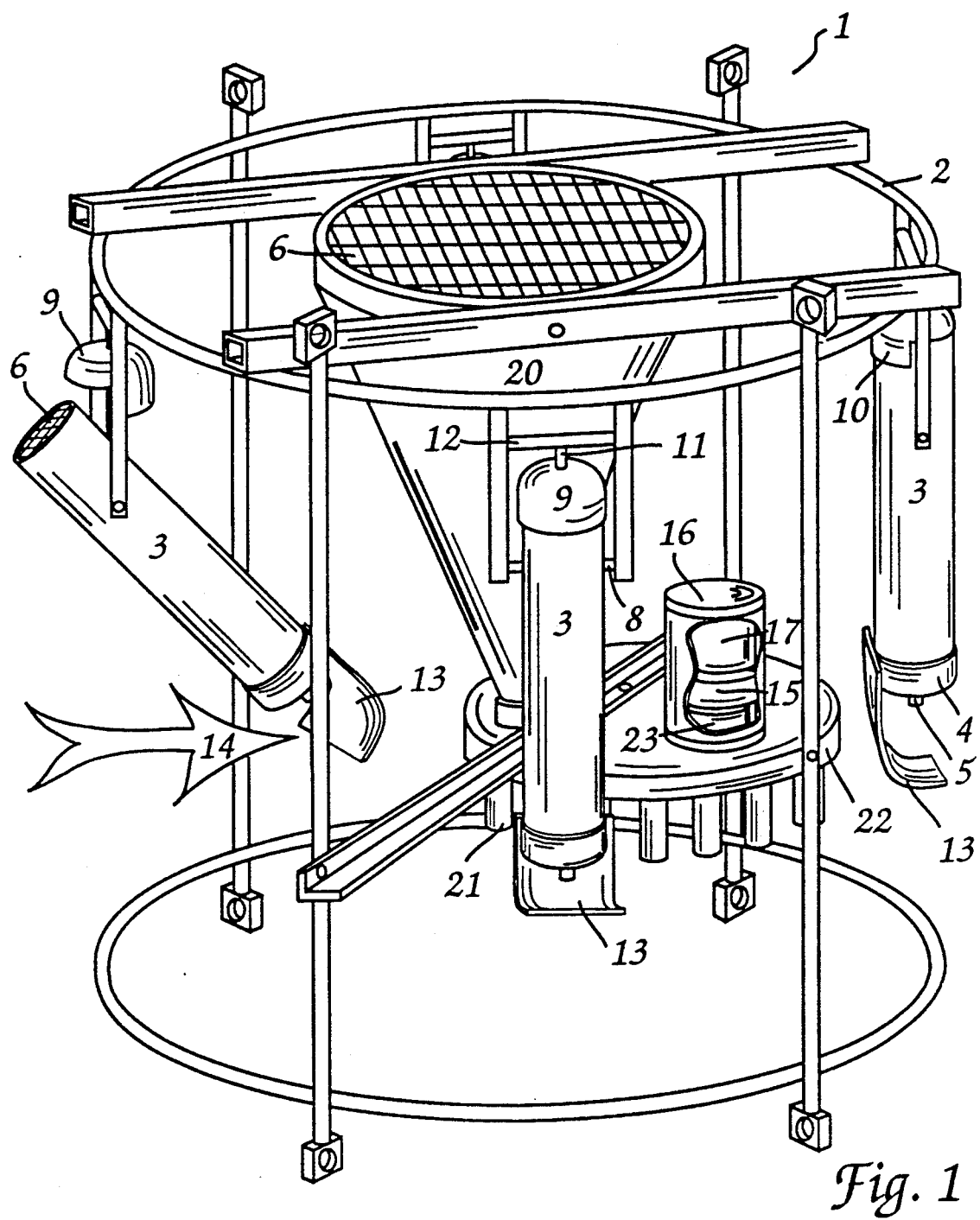
FIG. 1 is a perspective view, partially cut away, of a preferred embodiment of directional sediment and pollution monitor.

Referring to FIGS. 1–2, and to the general operation of the mechanism, the framework structure containing the array of sediment-vector tubes 3 is placed on the bottom of a body of water and oriented with respect to a known compass heading. Movement of a current of water 14 from a quadrant that faces the curved inner configuration of the current pressure vane 13 applies greater pressure to the lower part of the sediment-vector tube 3, thereby rotating the sediment-vector tube into the current from a vertical alignment, thereby unsealing and tilting the upper, open end of the sediment-vector tube. Materials and substances carried in the water current 14 are thereby allowed to pass through the multiple tubular cells and orifices 7 of the baffle 6 and enter the sediment-vector tube 3. Materials collected within the sediment-vector tube 3 are removed for analysis through the removable plug 5 in the end cap 4. Each individual sediment sediment-vector tube 3 within the array of sediment-vector tubes referred to in the aforementioned applications accumulates sediment only when said sediment-vector tube is held open by pressure from a current which moves in a restricted geographic direction. The free-swinging stop 10 applies greater pressure to the lower part of the sediment-vector tube 3 and the current-pressure vane 13 and pushes the upper, open end of the sediment-vector tube 3 against the closing cap 9, thereby sealing said tube. There is provided, therefore, a mechanism that collects material only from the direction from which a current moves, in proportion to the velocity of said current, and in proportion to the concentration of said materials in the moving body of water.

Referring now to an enhanced embodiment of the sampling device, and particularly to FIG. 1, a conventional electronic compass device unit 15 is mounted in a fixed position within a pressure case 16 that is rigidly mounted to an apparatus within the framework structure 2. Said compass device unit 15 is connected to a conventional timing-circuit and memory device unit 17, also contained within the aforementioned pressure case 16. The electronic compass device unit 15 measures the compass heading of the framework structure 2 and the array of sediment-vector tubes 3 and the compass heading is recorded by said timing-circuit and memory device unit 17 at short intervals of time throughout the period of deployment and operation. After retrieval of the directional sediment and pollution sampling device from the body of water, materials accumulated in the sediment-vector tubes 3 and corresponding data regarding the geographic heading that is stored in the timing-circuit and memory device unit 17 are recovered for study and analysis. The enhanced embodiment illustrated in FIG. 1 automatically measures the compass bearing of the framework structure as it rests on the bottom of a body of water under all conditions and does not require direct observation of the position or heading of the framework structure, thereby permitting deployment in remote, inaccessible locations. Periodic measurement of the heading of the framework structure 2 also provides information about the stability or the disturbance of the framework structure throughout the period of deployment, thereby assuring control of the quality of the data collected.

Referring now to FIG. 3, and to another enhanced embodiment of the aforementioned direction sediment and pollution monitor, the framework structure 2 is positioned above the bottom and within a water body between an upper swivel 18 and a lower swivel 18 and said structure is attached by cables to flotation and anchoring devices (not illustrated). Current-direction vanes 19 are rigidly affixed to the framework structure. Pressure exerted current 14 during the period of deployment. Materials collected in the sediment-vector tube in the quadrant of the framework structure that faces the direction from which the current moves provides information about the volume and composition of said materials carried laterally by said current 14. Sediments in Vector tubes 3 in the other quadrants are used to confirm orientation of framework structure 2 with respect to current direction during period of deployment or may be omitted in this mid-water application.

Referring again to FIGS. 1 and 3 and to still another and a further-enhanced embodiment of the directional sediment and pollution monitor, a large-diameter magnifying cone 20 is vertically mounted in the center of a framework structure 2. The magnifying cone 20 has a baffle 6 mounted within the larger end and the cone is connected at the lower end to small-diameter collecting tubes 21, thereby providing for a large ratio of magnification for the collection of a large volume of suspended material. The collecting tubes 21 are affixed to a rotatable carousel device 22. The collecting tubes 21 are rotated to a collecting position under the magnifying cone 20 for a predetermined interval of time by a conventional stepping motor and drive unit 23 contained within the pressure case 16. The timing and memory device unit 17 in the pressure case actuates the motor and drive unit 23 which rotates the carousel 22 and collecting tubes 21 to a position under the magnifying cone 20 at repeated and predetermined time intervals, thereby providing for the collection of many samples over an extended interval of time. The aforementioned timing-circuit and memory device unit 17, in conjunction with the electronic compass device unit 15, measures and records the compass bearing of the framework structure 2 at short, repeated, and predetermined time intervals, thereby providing a known compass bearing for the direction of current flow for the sample contained in each collecting tube 21.

Referring now to all the figures and to the combined operation of the sediment-vector tubes 3 and the magnifying cone 20 and collecting tubes 21, the framework structure 2 is mounted either in a fixed and known position on the bottom of a body of water, or the aforesaid structure 2 is mounted between swivels 18 within a body of water. In the bottom configuration, when used in conjunction with the continuous measurement of the compass heading of the framework structure 2, the samples facing the current combined with the use of a magnifying cone 20 and collecting tubes 21 provides information about the relative volume and composition of materials moving both laterally and downward within the water body. Samples contained in the collecting tube 21 provide additional data about the volume and composition of materials moving through the water body for short, discrete intervals of time.

The aforementioned devices and embodiments of the directional sediment and pollution monitor, used in conjunction with conventional devices that measure the compass heading and the accumulation of materials at short, regular time intervals, provide an efficient means for measuring vectors of transport and rate of movement of natural materials and polluting substances within bodies of water, for providing materials for analysis, and for identifying the source of said materials and substances. It can, therefore, be seen that the present directional sediment and pollution monitor serves to completely replace the inefficient structures of prior art collecting and measuring methods. Not only is the present apparatus more efficient by measuring the direction, rate of movement, and source of the materials carried by currents within a water body, in addition, by collecting samples in short time intervals, and by measuring the direction of orientation of the device for each time interval, the present directional sediment and pollution monitor provides a continuous record of the direction of movement of materials within a water body. The present directional sediment and pollution monitor has the added advantage of greatly reducing the number of sampling stations and the number of analyses required to trace the movement and source of natural and polluting substances.

While the invention has been described with respect to a preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

I claim:

1. A directional sediment and pollution monitor adapted to be positioned in a body of water comprising:
    a) an array of several collecting tubes mounted on a framework structure with said tubes having an open and a closed end, each tube adapted to accumulate materials entering each said tube from a restricted geographic direction,
    b) baffle means positioned adjacent the open end of each tube for minimizing turbulence, reducing loss of materials, and eliminating entry of large organisms,
    c) compass means mounted on said framework structure and structurally connected to monitor said tubes for measuring geographic orientation of said tubes, and
    d) recording means for storing measurements of said geographic orientation of said tubes at time intervals thereby providing materials for measuring the direction, quantity, and rate of movement of natural and polluting substances.

2. A directional sediment and pollution monitor according to claim 1 wherein said compass means comprises an electronic, flux-gate compass and timer.

3. A directional sediment and pollution monitor according to claim 1 wherein said time intervals are determined by a device comprising a conventional electronic timing circuit.

4. A directional sediment and pollution monitor according to claim 1 wherein the said recording means comprises an electronic memory circuit.

5. A directional sediment and pollution monitor according to claim 1 wherein said baffle means comprises a multiplicity of vertically aligned cells, each cell including an opening of a first size at the upper end and an opening of a second size at the lower end, the second size being smaller than the first size.

6. A directional sediment and pollution monitor adapted to be positioned in a body of water comprising;
    a) a framework structure with four quadrants and a pressure case mounted on said framework containing a conventional electronic timer circuit, a conventional electronic compass for providing compass bearings of vertically aligned and hinged collecting tubes mounted in each of said quadrants, each of said quadrants including at least one tube,
    b) baffle means adjacent the upper open end of each tube for reducing turbulence in said tubes, reducing escape of materials from said tubes and preventing entry of large organisms in said tubes,
    c) closure means adjacent the upper end of said tubes for sealing said tubes eliminating entry of materials during sampling;
    d) vane means mounted at the lower end of said tubes for tilting said tubes allowing entry of materials, and
    e) recording means for automatically storing compass bearings.

7. A directional sediment and pollution monitor adapted to be positioned in a body of water comprising:
    a) a framework structure with each quadrant having a vertically aligned and hinged tube covered by a closing means attached to said structure,
    b) a vertically aligned, funnel shaped magnifying cone mounted in the center of said framework structure connected at the lower smaller diameter end to a multiplicity of movable collecting vessels,
    c) baffle means adjacent the upper open end of the said hinged tubes and said magnifying cone for reducing turbulence in said tubes and said magnifying cone, for reducing escape of materials from said tubes and magnifying cone and for preventing entry of large organisms,
    d) compass means attached to said framework structure for providing compass bearings of said framework structure,
    e) vane and swivel means attached to said framework structure for orienting said framework structure within a current,
    f) moving means for automatically isolating material in said movable collection vessels at regular time intervals,
    g) measuring means attached to said framework structure for determining the compass bearings of said framework structure at regular time intervals, and
    h) recording means attached to said framework structure for automatically storing compass bearings of said framework structure at regular time intervals.

* * * * *